United States Patent [19]

Lartey et al.

[11] Patent Number: 5,217,960
[45] Date of Patent: Jun. 8, 1993

[54] ERYTHROMYCIN DERIVATIVES

[75] Inventors: Paul A. Lartey, Wadsworth; Ramin Faghih, Gurnee, both of Ill.; Shari DeNinno, Gales Ferry, Conn.

[73] Assignee: Abbott Laboratories, Abbott Park, Ill.

[21] Appl. No.: 695,176

[22] Filed: May 3, 1991

[51] Int. Cl.$^5$ .................. A61K 31/70; C07H 17/08
[52] U.S. Cl. .................. 514/29; 536/7.2; 536/7.4
[58] Field of Search .................. 519/29; 536/7.4, 7.2

[56] References Cited

U.S. PATENT DOCUMENTS 3,652,537  3/1972  Massey et al. .................. 536/7.2
4,826,820  5/1989  Brain .................. 514/29

OTHER PUBLICATIONS

Mauske et al, J. Org. Che., 48:5138 (1983).

Primary Examiner—Johnnie R. Brown
Assistant Examiner—Elli Peselev
Attorney, Agent, or Firm—Andreas M. Danckers

[57] ABSTRACT

Antibacterial compounds are disclosed having the formula

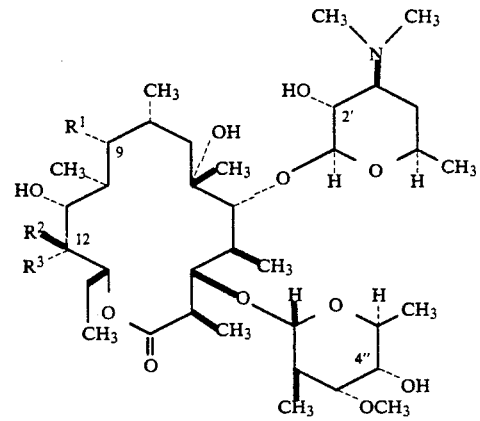

and pharmaceutically acceptable salts thereof, wherein $R^1$ is $-NR^4R^6$, where $R^4$ and $R^6$ are independently selected from the group consisting of hydrogen, loweralkyl and arylalkyl or, together, $R^4$ and $R^6$ form a nitrogen-containing heterocycle attached at the nitrogen atom; $R^2$ is selected from the group consisting of hydrogen, $-OH$ and, when $R^3$ is methylene, oxygen so as to form an epoxide; and $R^3$ is selected from the group consisting of $-CH_2OH$, $-NR^4R^6$, $-(CH_2)_nNR^4R^6$ and, when $R^2$ is oxygen, methylene so as to form an epoxide, where n is 1–4 and $R^4$ and $R^6$ are as previously defined, with the proviso that when $R^2$ is $-OH$, $R^3$ may not be $-NR^4R^6$; or $R^2$ and $R^3$ together are $=CH_2$. Also disclosed are processes and intermediates useful in the preparation of the above compounds, as well as compositions containing the same and methods for their use.

8 Claims, No Drawings

ERYTHROMYCIN DERIVATIVES

TECHNICAL FIELD

The present invention relates to novel semisynthetic macrolides having antibacterial activity and useful in the treatment and prevention of bacterial infections. More particularly, the invention relates to C-12,21-modified derivatives of (9R)-9-amino-9-deoxoerythromycin, processes for their preparation, compositions containing such compounds and methods for using the same.

BACKGROUND OF THE INVENTION

Erythromycins A through D, represented by formula (I),

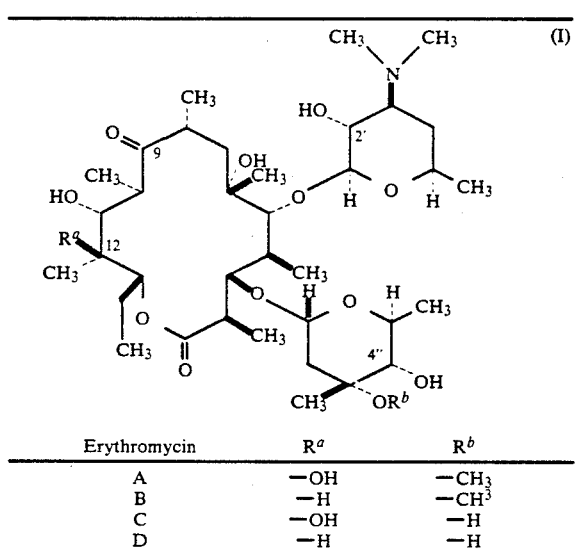

| Erythromycin | $R^a$ | $R^b$ |
| --- | --- | --- |
| A | —OH | —$CH_3$ |
| B | —H | —$CH_3$ |
| C | —OH | —H |
| D | —H | —H | are well-known and potent antibacterial agents. Erythromycin A in particular is widely used to treat and prevent bacterial infection. As with other antibacterials, however, bacterial strains having resistance or insufficient susceptibility to erythromycin have been identified. Consequently, numerous investigators have prepared chemical derivatives of erythromycin in an attempt to obtain analogs having modified or improved profiles of antibiotic activity.

Examples of such analogs include (9R)-9,9-dihydro-9,11-di-O-thiocarbonylerythromycin A, reported by Hauske et al. in *J. Org. Chem.*, 48:5138 (1983), and the 12,12'-anhydro-(9R)-hydroxy-9-deoxoerythromycin derivatives prepared therefrom according to Hauske in European Patent Application No. 303 471, published Feb. 15, 1989. These latter derivatives are characterized by the presence, in the final product or during synthesis, of $C_2$-$C_4$ alkanoate esters at the 4" position, and preferably of a 4" acetate group. Such substituents appear to result in a reduction of antibacterial activity, however, as well as a limitation upon the range of possible substituents at other positions when the 4" alkanoate moiety is ultimately removed.

Other analogs of erythromycin include those in which the ketone at position 9 is substituted with an amine as in (9S)-9-amino-9-deoxoerythromycin A (erythromycylamine), described by Massey et al. in U.S. Pat. No. 3,652,537, issued Mar. 28, 1972. 9-N-substituted derivatives of these analogs have also been reported, as by Bonjoukliah et al. in European Patent Application No. 238 178, published Sep. 23, 1987, by Pariza et al. in European Patent 345 627, published Dec. 13, 1989, and by Maring et al. in 29th ICACC, Abstr. 1023–1025, 1989 (disclosing azacyclic derivatives). There has been no suggestion, however, of the further functionalization of 9-N-substituted derivatives by modification at C-12 and C-21.

SUMMARY OF THE INVENTION

The present invention comprises novel derivatives of erythromycin having the formula

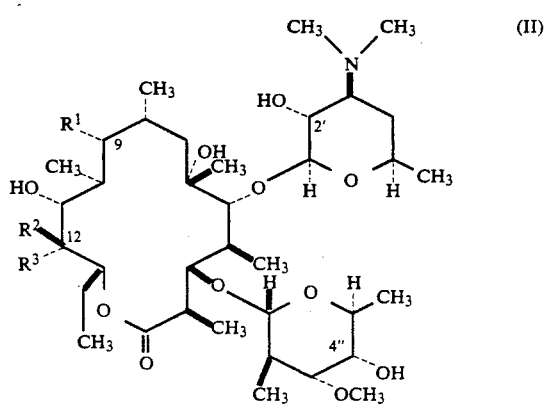

and pharmaceutically acceptable salts thereof. In formula (II), $R^1$ is —$NR^4R^6$ where $R^4$ and $R^6$ are independently selected from the group consisting of hydrogen, loweralkyl and arylalkyl or, together, form a nitrogen-containing heterocycle attached at the nitrogen atom. Also in formula (II), $R^2$ may be hydrogen or —OH, while $R^3$ may be selected from the group consisting of —$CH_2OH$, —$NR^4R^6$ and —$(CH_2)_nNR^4R^6$, where n is 1-4 and $R^4$ and $R^6$ are as defined above, with the proviso that when $R^2$ is —OH, $R^3$ may not be —$NR^4R^6$. Alternatively, $R^3$ may be methylene and $R^2$ an oxygen atom which, together with C-12, form an epoxide. These compounds are shown to possess antibacterial activity against a variety of pathogens.

The present invention also comprises synthetic processes for the preparation of the compounds of the invention, as well as novel intermediates useful therein which have the formula

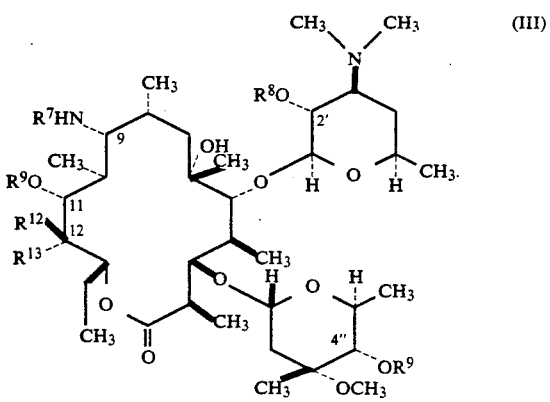

In formula (III), $R^7$ is hydrogen or a first suitable protecting group, such as a carbobenzyloxycarbonyl; $R^8$ is hydrogen or a second suitable protecting group, such as acetyl; and $R^9$ is hydrogen or a third, readily removable protecting group, such as formyl, with the proviso that at least one of $R^7$, $R^8$ and $R^9$ must be other than hydrogen. Also in formula (III), $R^{12}$ and $R^{13}$ may together be a single carbon atom double-bonded to C-12. Alternatively, $R^{13}$ may be methylene and $R^{12}$ an oxygen atom which, together with C-12, form an epoxide.

The intermediates of formula (III) are prepared by the selective protection of various reactive sites of (9R)-erythromycylamine, followed by dehydration to form a C-12,21 double bond and, optionally, by epoxidation at that location. These intermediates are readily converted, by deprotection and by further derivatization at positions 9 and 12/21, into the compounds of formula (II).

Because of their antibacterial activity, it is anticipated that the compounds of the present invention will be useful as pharmaceutical agents or industrial disinfectants. Accordingly, the invention also comprises compositions useful in the treatment and prevention of bacterial infection, comprising a therapeutically effective amount of a compound of formula (II) in combination with a pharmaceutically acceptable carrier.

The present invention further comprises a method for treating and preventing bacterial infections in humans and other mammals, comprising administering to a patient in need of such treatment a therapeutically effective amount of a compound of the invention for such time as is necessary to achieve the desired therapeutic effect.

DETAILED DESCRIPTION OF THE INVENTION

In one aspect of the present invention are disclosed compounds of the formula

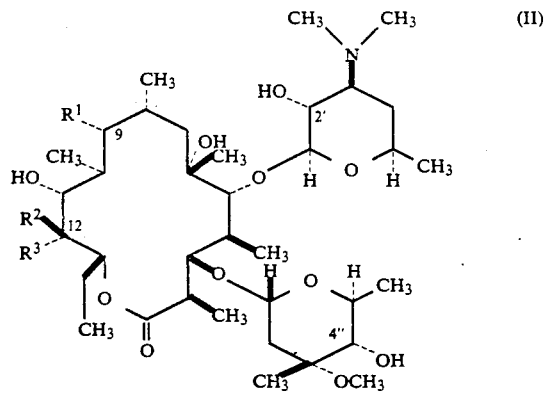

and pharmaceutically acceptable salts thereof, wherein $R^1$ is $-NR^4R^6$, where $R^4$ and $R^6$ are independently selected from the group consisting of hydrogen, lower-alkyl and arylalkyl or, together, $R^4$ and $R^6$ form a nitrogen-containing heterocycle attached at the nitrogen atom; $R^2$ is selected from the group consisting of hydrogen, $-OH$ and, when $R^3$ is methylene, oxygen so as to form an epoxide; and $R^3$ is selected from the group consisting of $-CH_2OH$, $-NR^4R^6$, $-(CH_2)_nNR^4R^6$ and, when $R^2$ is oxygen, methylene so as to form an epoxide, where n is 1-4 and $R^4$ and $R^6$ are as previously defined, with the proviso that when $R^2$ is $-OH$, $R^3$ may not be $-NR^4R^6$; or $R^2$ and $R^3$ together are $=CH_2$.

Representative examples of the compounds of the present invention include the following: (9R)-9-deoxo-9-(N,N-dimethylamino)-12,21-epoxyerythromycin A, (9R)-9-deoxo-9-(N,N-dimethylamino)-21-hydroxyerythromycin A, (9R)-9-deoxo-9-(N,N-dimethylamino)-21-hydroxyerythromycin B, (9R)-9-amino-21-benzylamino-9-deoxoerythromycin A, (9R)-9,21-diamino-9-deoxoerythromycin A, 9R)-21-(N-benzyl-N-methylamino)-9-deoxo-9-(N,N-dimethylamino)-erythromycin A, (9R)-9-deoxo-9-(N,N-dimethylamino)-21-(N-methylamino)-erythromycin A, and (9R)-9,21-di-(N,N-dimethylamino)-9-deoxoerythromycin A.

Of these, a preferred example of the compounds of the invention is (9R)-9-deoxo-9-(N,N-dimethylamino)-12,21-epoxyerythromycin A.

In a second aspect of the present invention are intermediates useful in the preparation of the above compounds and having the formula

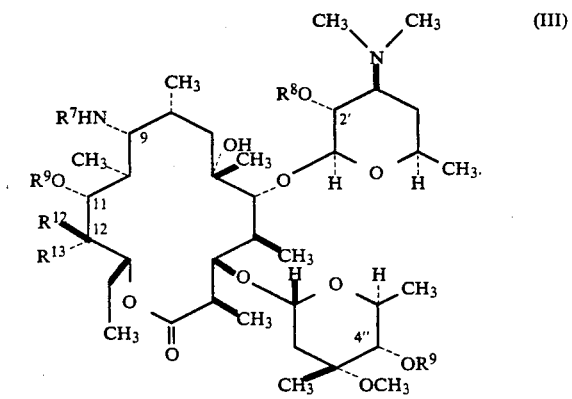

wherein $R^7$ is hydrogen or a first suitable protecting group, $R^8$ is hydrogen or a second suitable protecting group, and $R^9$ is hydrogen or a third, readily removable protecting group, with the proviso that at least one of $R^7$, $R^8$ and $R^9$ must be other than hydrogen; and $R^{12}$ is an oxygen atom and $R^{13}$ is methylene so as to form an epoxide, or $R^{12}$ and $R^{13}$ together are $=CH_2$.

Representative examples of the intermediates of the invention include: (9R)-9-(N-carbobenzyloxyamino)-12,21-dehydro-9-deoxoerythromycin A, (9R)-2'-O-acetyl-9-(N-carbobenzyloxyamino)-12,21-dehydro-9-deoxoerythromycin A, (9R)-2'-O-acetyl-9-(N-carbobenzyloxyamino)-9-deoxo-12,21-epoxyerythromycin A, and (9R)-9-(N-carbobenzyloxyamino)-9-deoxo-12,21-epoxyerythromycin A.

As used herein, the term "pharmaceutically acceptable salts" refers to those salts which are, within the scope of sound medical judgment, suitable for use in contact with the tissues of humans and lower animals without undue toxicity, irritation, allergic response and the like, commensurate with a reasonable risk-to-benefit ratio, and effective for their intended use in the chemotherapy and prophylaxis of antimicrobial infections. Pharmaceutically acceptable salts are well known in the art. For example, S. M. Berge, et al. describe pharmaceutically acceptable salts in detail in *J. Pharmaceutical Sciences*, 66: 1–19 (1977). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, alginate, cyclopentanepropionate, digluconate, dodecylsulfate, ethanesulfonate, hemisulfate, heptanoate, hexanoate, 2-naphthalenesulfonate, pamoate, persulfate, pivalate, propionate, undecanoate salts and the like, and they may be prepared according to conventional methods. Representative alkali or alkaline earth metal salts include sodium, calcium, potassium, magnesium salts and the like. Further pharmaceutically acceptable salts include, when appropriate, quaternary ammonium salt compounds formed using counterions such as halide, hydroxide, carboxylate, sulfate, phosphate, nitrate, loweralkyl sulfonate and arylsulfonate.

As used herein, the term "loweralkyl" refers to a straight and branched chain radical containing one to six carbon atoms including, but not limited to, methyl, ethyl, n-propyl, isopropyl, n-butyl, tert-butyl and the like.

As used herein, the term "arylalkyl" refers to an aromatic cyclic or bicyclic radical including, but not limited to, phenyl, 1-naphthyl, 2-naphthyl and the like connected via an intervening loweralkyl group as defined above.

As used herein, the term "heterocycle" refers to a five-, six- or seven-membered ring structure containing carbon atoms and one or two ring heteroatoms selected from the group consisting of nitrogen, oxygen and sulfur including, but not limited to, piperidinyl, morpholinyl, hexahydroazepinyl, azetidinyl, aziridinyl, pyrollidinyl and piperazinyl. Such groups may optionally be substituted with one or two radicals independently selected from the group consisting of methyl, ethyl, methoxy, amino, halo (including fluoro, chloro, bromo and iodo), hydroxy, nitro, cyano and the like.

In another aspect of the present invention are disclosed pharmaceutical compositions comprising a therapeutically effective amount of a compound of the invention and a pharmaceutically acceptable carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution ethyl alcohol, and phosphate buffer solutions, as well as other nontoxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such exipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

In a further aspect of the present invention is disclosed a method for treating or preventing bacterial infections in a human or lower mammal, comprising administering to a patient in need of such treatment or prophylaxis a therapeutically effective amount of a compound of the invention, for such time as is necessary to achieve a therapeutic effect. By a "therapeutically effective amount" of the compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 to about 1000 mg of the compound(s) of this invention per day in multiple doses or in a single dose of from 10 mg to 1000 mg.

In yet another aspect of the present invention are disclosed processes useful in the preparation of the above compounds. In general, a 9-amino-9-deoxo derivative of erythromycin having a 9-N-protecting group is treated by first protecting the 11- and 4"-hydroxyl groups of the derivative with a readily removable protecting group to form a first protected compound, dehydrating the same to form a second protected compound having a C-12,21 double bond, and then deprotecting the second compound to form a third having unprotected 11- and 4"-hydroxyl groups and a C-12,21 double bond and retaining the 9-N-protecting group. The resulting 11- and 4"-hydroxyl intermediate is readily modified to obtain the antibacterial compounds of the present invention.

Representative of the processes of the invention are reaction schemes I through III, presented below. In Scheme I, (9R)-9-amino-9-deoxo-erythromycin A 2 is 9-N protected using an activated carbonyl reagent, and selectively 2'-O protected by treatment with an acid anydride in a neutral inert solvent such as methylene or ethylene chloride. The 11- and 4"-hydroxyl groups of the resulting carbamate 3 are then protected with a readily removable moiety such as a formate, using an anhydride of formic acid under base catalysis in an inert solvent. The protected product 4 is next treated with an activating reagent such as a sulfonyl or thionyl chloride in the presence of an organic base, as for example a trialkylamine or an arylalkylamine such as tribenzylamine, to effect elimination of the activated hydroxyl group at C-21 and formation of the 12,21-double bond. This product is then de-protected at positions 2', 4" and 11 to facilitate purification of the intermediate 5.

After re-protection of the 2'-hydroxyl group, the resulting compound 6 is treated with an epoxidizing oxidant such as peroxide in an inert solvent, followed by a mild reducing agent such as triphenylphosphine to convert any 3'-N-oxides, formed in the presence of the oxidant, back to amines. The epoxide 7 is next subjected to prolonged catalytic hydrogenation under N-alkylation conditions, as for example in the presence of an aldehyde, leading to the removal of the 9-N-protecting group and alkylation of the 9-amine. If such a reaction is allowed to proceed under transesterification conditions, such as in the presence of a low molecular weight alcohol, concomitant removal of the 2'-hydroxyl protecting group occurs. The choice of aldehyde determines the resulting alkyl group substitution of the 9-amine in the product 8; for example, formalin leads to an N,N-dimethyl substitution at C-9, while dialdehydes of the structure C(O)H—X—C(O)H lead to the formation of heterocyclic 9-amines having the structure

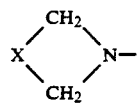

where X may be any intervening alkyl or hetero-substituted alkyl chain, either straight or branched.

Other compounds of the present invention may be prepared according to reaction Scheme II, in which the double bond of the 2′-protected intermediate 6, above, is oxidized as, for example, by osmylation with OsO$_4$ or treatment with KMnO$_4$, followed by removal of the 2′-O-acetate under mild conditions such as refluxing in methanol. The resulting intermediate 9 is then deprotected at position 9 with concomitant N-alkylation to provide the dimethylamine derivative 10. Alternatively, the 2′-protected intermediate 6 may be treated by hydroboration of the C-12,21 double bond followed by the selective installation, utilizing oxidative conditions, of a hydroxyl group at position 21. This product is then partially purified prior to the removal of the 2′-protecting group under mild conditions, after which the material is again partially purified and the 9-N protecting group removed with concomitant reductive alkylation of the 9-amine to afford the compound 11.

Beginning with the epoxide intermediate 7, still other compounds of the invention may be prepared according to reaction Scheme III. After removal of the 2′-O-acetate protecting group by refluxing with methanol under neutral conditions, the deprotected intermediate 12 is treated with an appropriate nucleophile such as an amine, carbanion or thiol, under catalysis by a mild acid or Lewis acid, to open the epoxide ring. An example is the regioselective opening of 12 by benzylamine, catalyzed by alumina, to produce the C-21 benzylamine derivative 13.

Where identical amino-substitutions at C-9 and C-21 are desired, the intermediate 13 may be subjected to extended hydrogenolysis to remove both the 9-N-benzyloxycarbonyl and the 21-N-benzyl protecting groups. The deprotected primary amines are then reductively alkylated, such as by using catalytic hydrogenation in the presence of an aldehyde or dialdehyde, to form the product 18 having the same alkyl groups or cyclic substitutions at each amine. Alternatively, a shorter hydrogenolytic treatment of intermediate 13 results in a good yield of a partially deprotected 21-N-benzyl product 14 which may then be reductively alkylated to afford the assymetric amino-substituted product 16. If desired, the N-benzyl moiety may then be removed to produce the product 17, or the 21-amine may be further alkylated.

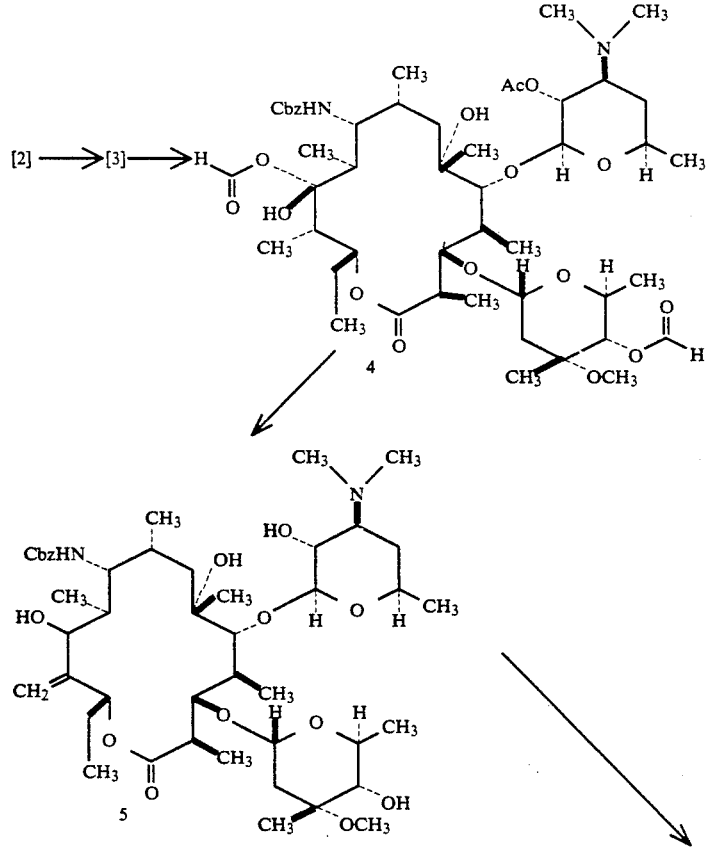

Scheme 1

-continued
Scheme 1
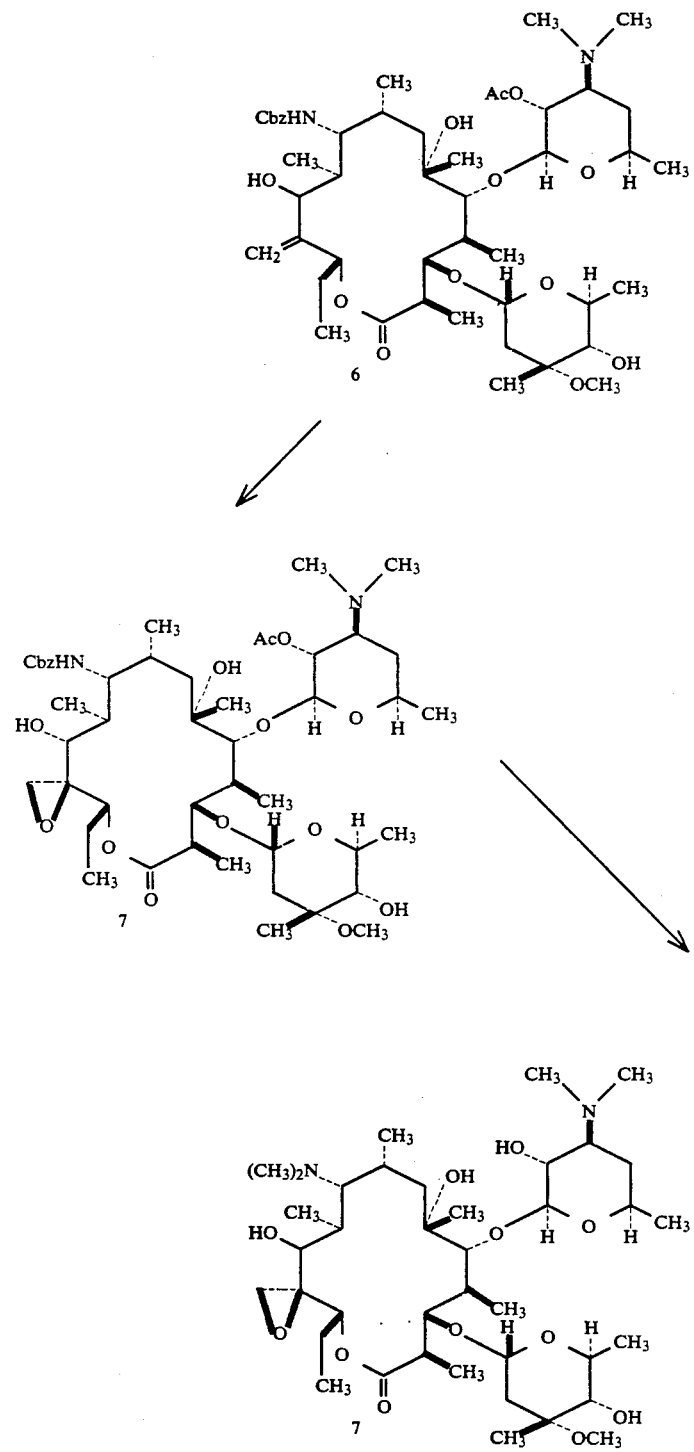

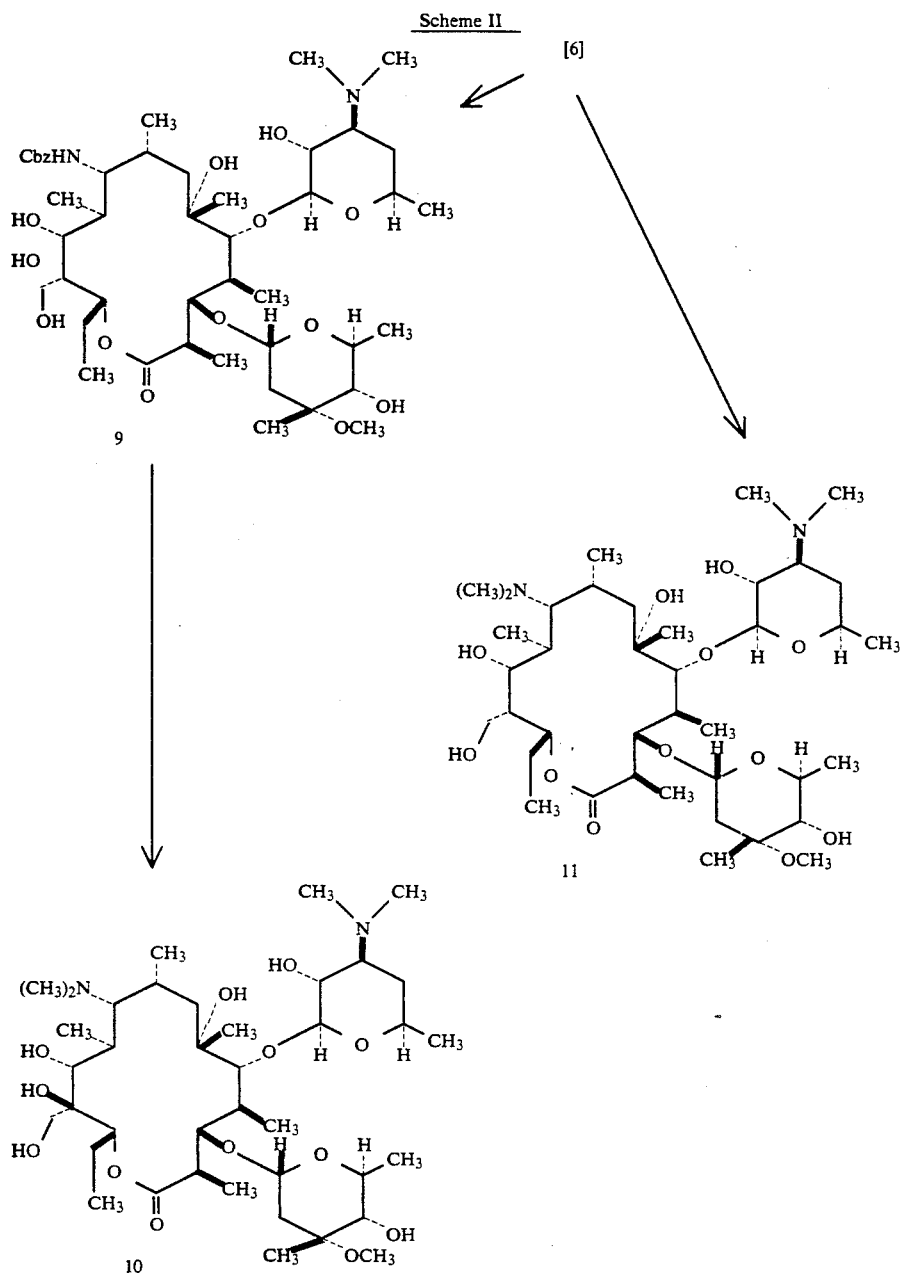
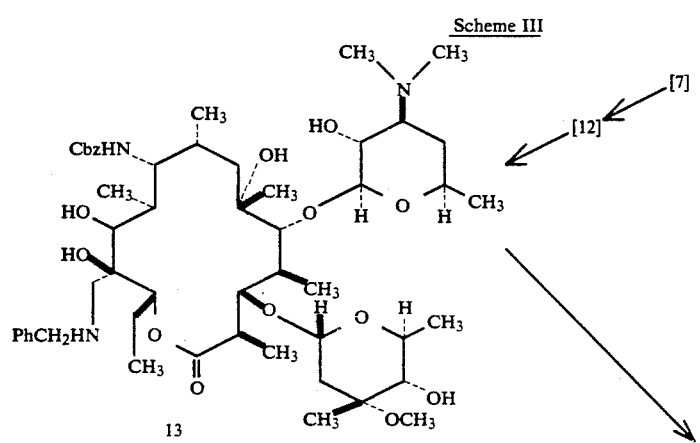

Scheme III -continued

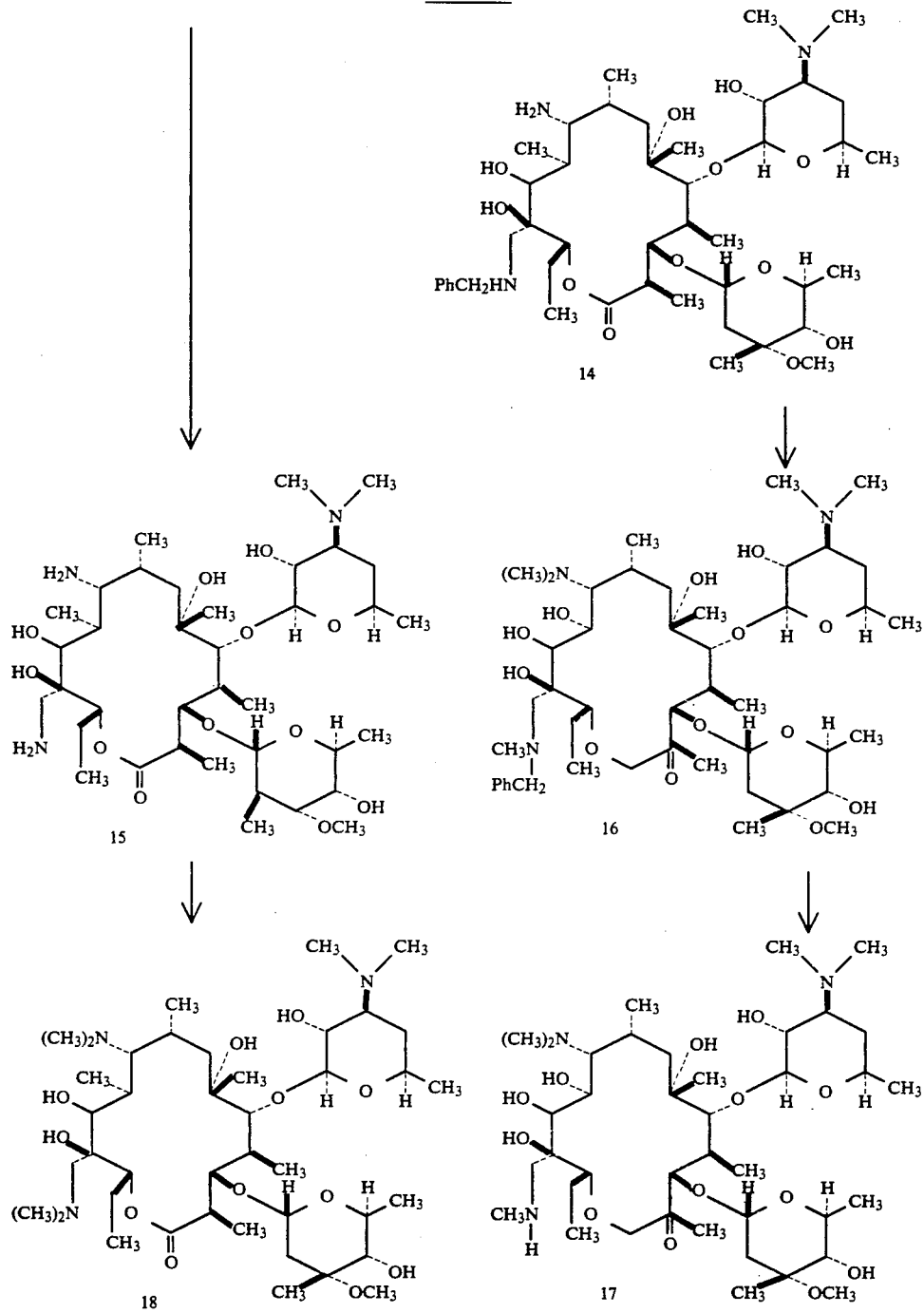

The above processes for preparing the compounds of the present invention will be better understood in connection with the following examples, which are intended as an illustration of and not a limitation upon the scope of the invention.

EXAMPLE 1

(9R)-2'-O-acetyl-9-(N-carbobenzyloxyamino)-9-deoxoerythromycin A

N-(Benzyloxycarbonyloxy)succinimide (7.1 g, 28.61 mmol) was added to (9R)-erythromycylamine 2 (20 g, 27.25 mmol) in 200 mL of $CH_2Cl_2$ at room temperature. After 1.5 hours, the solution congealed into a white mass. The solution was diluted with 200 mL $CH_2Cl_2$ and, after four hours, Thin layer chromatography (TLC) showed the reaction to be complete. Saturated sodium bicarbonate solution (200 mL), $CH_2Cl_2$ (200 mL) and methanol (100 mL) were added, stirred and the insoluble material filtered off. The filtrate was concentrated and the remaining aqueous layer washed with $CH_2Cl_2$ (3×50 mL). The combined organic phase was washed with brine (100 mL) and dried over $MgSO_4$ and filtered. The filtrate was concentrated and the residue chromatographed over silica gel (5% MeOH/0.5%

NH$_4$OH in CH$_2$Cl$_2$ followed by 10% MeOH/1% NH$_4$OH in CH$_2$Cl$_2$) to yield 22.4 g (94%) of desired 9-carbobenzyloxylamino intermediate. Acetic anhydride (2.5 mL, 0.027 mole) was added to a solution of a portion of the intermediate (21 g, 0.024 mole) in 400 mL dry CH$_2$Cl$_2$ at room temperature. The reaction was stirred for four hours and the CH$_2$Cl$_2$ removed in vacuo. The excess acetic anhydride was removed on a high vacuum pump to give 19 g (87%) of compound 3 as a white foam: mp 149°–151° C.; $[\alpha]_D$ −49.6° (c 1.0, CHCl$_3$); MS m/e 911 (M$^+$+1); Anal. (C$_{47}$H$_{78}$N$_2$O$_{15}$.2-H$_2$O) C, H, N.

EXAMPLE 2

(9R)-2'-O-acetyl-9-(N-carbobenzyloxyamino)-9-deoxo-4",11-O-diformylerythromycin A Dimethylaminopyridine (4.3 g, 35.4 mmol) was added to a stirring solution of 3 (16.6 g, 17.7 mmol) in 100 mL CH$_2$Cl$_2$ at 0° C. Formic acetic anhydride (2.8 mL, 35.4 mmol) was added drop-wise. After fifteen minutes, the solution was warmed to room temperature and allowed to stir for forty-eight hours. The reaction was quenched with saturated sodium bicarbonate solution (100 mL) and extracted with CH$_2$Cl$_2$ (3×50 mL). The organic layer was washed with brine (100 mL), dried (MgSO$_4$) and the solution concentrated. The crude residue was redissolved in CH$_2$Cl$_2$ and washed with 10% aqueous HCl solution (50 mL). The aqueous layer was adjusted to pH 9 with NH$_4$OH and extracted with CH$_2$Cl$_2$ (3×50 mL). The combined CH$_2$Cl$_2$ extracts were dried (MgSO$_4$) and concentrated. The crude residue was redissolved in a minimum amount of THF and diluted with 5% NaH$_2$PO$_4$ solution. This homogeneous solution (pH=5) was stirred for 20 minutes at room temperature, diluted with CH$_2$Cl$_2$ and extracted (3×50 mL), dried (MgSO$_4$) and concentrated to give 15.0 g (88%) of compound 4 as a white foam: $[\alpha]_D$ −59.0° (c 3.4, CHCl$_3$); MS m/e 967 (M$^+$+1).

EXAMPLE 3

(9R)-9-(N-carbobenzyloxyamino)-12.21-dehydro-9-deoxo-erythromycin A

Triethylamine (1.15 mL, 8.28 mmol) was added to a solution of 4 (2.0 g, 2.07 mmol) in 20 mL dry ethyl acetate at 0° C. Thionyl chloride (0.17 mL, 2.28 mmol) was added rapidly via syringe. After thirty minutes at 0° C., the reaction was quenched with saturated sodium bicarbonate solution and extracted sequentially with CH$_2$Cl$_2$ (3×20 mL) and ethyl acetate (30 mL). The combined extracts were washed with brine (50 mL), dried (MgSO$_4$), filtered and concentrated. The crude residue was chromatographed over silica gel (1:1 hexanes/acetone) to yield 1.29 g (55%) of a 2'-O-acetate protected intermediate as a white foam. Triethylamine (0.441 mL, 3.17 mmol) was added to a solution of a portion of the intermediate (600 mg, 0.633 mmol) in 10 mL MeOH. The solution was heated to reflux and allowed to stir for 18 hours, was cooled to room temperature and concentrated in vacuo. The crude residue was chromatographed over silica gel (3% MeOH/0.5% NH$_4$OH in CH$_2$Cl$_2$ followed by 6% MeOH/0.5% NH$_4$OH in CH$_2$Cl$_2$) to yield 407 mg (76%) of the desired intermediate 5 as a foam: $[\alpha]_D$ −39.6° (c 1.3, CHCl$_3$); MS m/e 851 (M$^+$+1); Anal. (C$_{45}$H$_{74}$N$_2$O$_{13}$.H$_2$O) C, H, N.

EXAMPLE 4

(9R)-2'-O-acetyl-9-(N-carbobenzyloxyamino)-12.21-dehydro-9-deoxo-erythromycin A

Acetic anhydride (35 μL, 0.373 mmol) was added to a solution of 5(317 mg, 0.373 mmol) in 8 mL dry CH$_2$Cl$_2$. The reaction was stirred for 20 hours and the product concentrated. The residue was chromatographed over silica gel (3% MeOH/0.5% NH$_4$OH in CH$_2$Cl$_2$) to yield 365 mg (89%) of a compound 6 as a white foam: $[\alpha]_D$ −38.53° (c 1.2, CHCl$_3$), MS m/e 895 (M$^+$+1); Anal. (C$_{47}$H$_{76}$N$_2$O$_{14}$.H$_2$O) C, H, N.

EXAMPLE 5

(9R)-2'-O-acetyl-9-(N-carbobenzyloxyamino)-9-deoxo-12.21-epoxy-erythromycin A

Metachloroperoxybenzoic acid (73%) (267 mg, 1.13 mmol) was added to a solution of 6 (336 mg, 0.377 mmol) in 8 mL CH$_2$Cl$_2$ at room temperature. The solution was stirred for four hours and the excess oxidant quenched with cyclohexene (76 μL, 0.754 mmol). The solution was stirred for fifteen minutes, quenched with saturated sodium bicarbonate solution and extracted with CH$_2$ (3×25 mL). The organic phase was washed with brine, dried (MgSO$_4$) and the solution filtered and concentrated. The crude product was chromatographed over silica gel (5% MeOH/0.5% NH$_4$OH in CH$_2$Cl$_2$ followed by 10% MeOH/1% NH$_4$OH in CH$_2$Cl$_2$) to yield 271 mg (78%) of a white foam. Triphenylphosphine (581 mg, 2.22 mmol) was added to a stirring solution of the white foam (293 mg, in 10 mL CH$_2$Cl$_2$ at room temperature. The reaction was stirred for 24 hours and quenched with saturated sodium bicarbonate solution. The mixture was extracted with CH$_2$Cl$_2$ (3×25 mL) and ethyl acetate (30 mL). The combined organic layers was washed with brine (50 mL), dried over MgSO$_4$, filtered and concentrated. The crude residue was chromatographed over silica gel (3% MeOH/0.5% NH$_4$OH in CH$_2$Cl$_2$) to yield 231 mg (80%) of compound 7 as a white foam: $[\alpha]_D$ −43.3° (c 1.2, CHCl$_3$); MS m/e (M$^+$); Anal. (C$_{47}$H$_{76}$N$_2$O$_{14}$.H$_2$O) C, H, N.

EXAMPLE 6

(9R)-9-deoxo-9-(N,N-dimethylamino)-12.21-epoxyerythromycin A

Formalin (37%) (45 μL, 1.6 mmol) was added to a solution of 7 (139 mg, 0.161 mmol) in 5 mL MeOH. Palladium on carbon catalyst (10%) (50 mg) was added and the mixture hydrogenated at 1 atmosphere for 5 hours. The reaction mixture was flushed with nitrogen, filtered through a plug of celite and the catalyst washed repeatedly with CH$_2$Cl$_2$ and MeOH. The combined filtrate and washings were concentrated and the residue chromatographed over silica gel (10% MeOH/1% NH$_4$OH in CH$_2$Cl$_2$) to yield 64 mg (53%) of desired product 8: $[\alpha]_D$ −51.85° (c 1.4, CHCl$_3$); MS m/e 761 (M$^+$+1); Anal. (C$_{39}$H$_{72}$N$_2$O$_{12}$.H$_2$O) C, H, N.

EXAMPLE 7

(9R)-2'-O-acetyl-9-(N-carbobenzyloxyamino)-9-deoxo-21-hydroxy-erythromycin A

Osmium tetroxide solution (2.5% in t-BuOH) (1.78 mL, 0.142 mmol) was added to a solution of 6 (115 mg, 0.29 mmol) in THF at room temperature. The solution was stirred for 24 hours and diluted with water. Florisil® activated magnesium silicate (Aldrich, Milwaukee, Wis.) (0.2 g) and excess solid sodium dithionite were added and the mixture stirred for two hours. The solution was diluted with a further 30 mL of water and the pH adjusted to 9 with NH4OH. The mixture was washed with EtOAc (3×30 mL) and brine (50 mL), dried (MgSO4) and concentrated. The residue was chromatographed over silica gel (3% MeOH/0.05% NH4OH in CH2Cl2) to yield 50 mg (42%) of the 2'-O-acetylated intermediate as a white solid. A portion 120 mg (0.129 mmol) of the intermediate was heated to reflux in 5 mL MeOH and allowed to stir for 24 hours. The solution was then concentrated and the crude product chromatographed over silica gel (5% MeOH/0.5% NH4OH in CH2Cl2 followed by 10% MeOH/1% NH4OH in CH2Cl2) to yield 74 mg (65%) of the product 9. $[\alpha]_D-39.0°$ (c 1.4, CHCl3); MS m/e 885 (M+); Anal. ($C_{45}H_{76}N_2O_{15}\cdot H_2O$) C, H, N.

EXAMPLE 8

(9R)-9-deoxo-9-(N,N-dimethylamino)-21-hydroxyerythromycin A

Formalin (37%) (15 mL, 0.532 mmol) was added to a solution of 9 (47 mg, 0.053 mmol) in 2 mL MeOH at room temperature. Palladium on carbon (10%) (50 mg) catalyst was added and the mixture hydrogenated for five hours at 1 atm. The mixture was filtered through a bed of celite and was washed well with CH2Cl2 and MeOH. The combined filtrate and washings were concentrated and the residue dissolved in 5% Na2HPO3 buffer (pH=5). After five minutes, the pH of the solution was adjusted to 9 with NH4OH and extracted with ethyl acetate (3×50 mL). The combined organic extracts were washed with brine (50 mL), dried (MgSO4) and concentrated. The residue was chromatographed over silica gel (5% MeOH/0.5% NH4OH in CH2Cl2 followed by 10% MeOH/1% NH4OH in CH2Cl2) to yield 25 mg (61%) of 10 as a white solid: $[\alpha]_D 44.90°$ (c 1.6, CHCl3); MS m/e 779 (M+1).

EXAMPLE 9

(9R)-9-deoxo-9-(N,N-dimethylamino)-21-hydroxyerythromycin B

Borane-THF (1M BH3 solution in THF) (2.9 mL, 2.86 mmol) was added to a stirring solution of 6 (255 mg, 0.286 mmol) in 6 mL THF at 0° C. The solution was warmed to room temperature and allowed to stir for 18 hours. The reaction was carefully quenched with 15 mL water and 10% KOH solution added drop-wise until the pH was 8. Hydrogen peroxide (30% w/v) (0.29 mL, 2.86 mmol) was added via syringe and the solution stirred for two hours. The solution was further diluted with 20 mL of water and adjusted to pH=9.5. The aqueous solution was extracted with EtOAc (3×20 mL) and the EtOAc extract washed with brine (50 mL). The organic layer was dried (MgSO4) and the solution concentrated.

The resulting residue was redissolved in MeOH, heated to reflux for 20 hours and methanol removed in vacuo. The residue was adhered onto silica gel and chromatographed over silica gel (5% MeOH/0.5% NH4OH in CH2Cl2) to yield 160 mg of a mixture of two products, which was carried further. Palladium on carbon catalyst (10%) (50 mg) was added to a stirring solution of the mixture of products from above (160 mg) in MeOH (5 mL) under nitrogen. The flask was evacuated and the mixture hydrogenated at 1 atmosphere for thirty minutes, filtered and the residue washed well with CH2Cl2 and MeOH. The combined filtrate and washings were concentrated and the residue chromatographed over silica gel (10% MeOH/1% NH4OH in CH2Cl2 followed by 20% MeOH/2% NH4OH in CH2Cl2) to give 80 mg of a mixture containing the desired intermediate. Formalin (37%) (162 mL, 2.17 mmol) was added to a stirring solution of the intermediate (80 mg, 0.108 mmol) in MeOH (5 mL) at room temperature. Palladium on carbon catalyst (10%) (50 mg) was added under nitrogen and the flask evacuated. The solution was stirred under hydrogen at 1 atmosphere for five hours. The catalyst was filtered off and washed with CH2Cl2 and MeOH. The combined filtrate and washings were concentrated and the residue chromatographed over silica gel (7% MeOH/0.5% NH4OH in CH2Cl2) to yield 55 mg (25% overall for 3 steps) of the compound 11 as a white solid: $[\alpha]_D-41.7°$ (c 0.9, CHCl3); HRMS calcd for $C_{39}H_{74}N_2O_{12}$ (MH+) 763.5320, found 763.5321.

EXAMPLE 10

(9R)-9-(N-carbobenzyloxyamino)-9-deoxo-12,21-epoxy-erythromycin A

The product of Example 5 7 (316 mg, 0.348 mmol) was dissolved in 5 mL of methanol, heated to reflux and the solution was allowed to stir overnight. The solution was concentrated under reduced pressure and immediately chromatographed over silica gel (5% MeOH, 0.5% NH4OH in CH2Cl2) to yield 294 mg (98%) of example 12: $[\alpha]_D-39.61°$ (c 0.95, CHCl3); MS m/e 867 (M+1)

EXAMPLE 11

(9R)-21-(N-benzylamino)-9-(N-carbobenzyloxyamino)-9-deoxoerythromycin A

Neutral alumina (922 mg) was added to a stirring solution of 12 (256 mg, 0.295 mmol) in 5 mL methoxyethanol at room temperature. Benzylamine (324 μL, 2.96 mmol) was added and the solution was warmed to reflux. After stirring overnight the solution was cooled to room temperature and diluted with 5% NaH2PO4 solution (20 mL). The layers were separated and the aqueous layer was extracted with methylene chloride (3×20 mL). The combined organic extracts were washed with brine (1×25 mL), dried over (MgSO4) and concentrated under reduced pressure. The crude product was chromatographed over silica gel (5% MeOH, 0.5% NH4OH in CH2Cl2) to yield 198.5 mg (70%) of compound 13: $[\alpha]_D-36.8°$ (c 2.3, CHCl3); MS m/e 974 (M+1); Anal. ($C_{52}H_{53}N_3O_{14}$) C, H, N.

EXAMPLE 12

(9R)-9-amino-21-benzylamino-9-deoxo-erythromycin A and (9R)-9,21-diamino-9-deoxo-erythromycin A Palladium on carbon catalyst (10%) was added to a stirring solution of 13 (128 mg, 0.132 mmol) in 3 mL MeOH under a nitrogen atmosphere at room temperature. The solution was hydrogenated for four hours and the reaction monitored to completion by TLC. The catalyst was filtered off under nitrogen and washed repeatedly with an excess MeOH and CH2Cl2. The combined filtrate and washings were concentrated and the residue redissolved in water; the pH of the solution was then adjusted to 9 with NH4OH. The aqueous solution was extracted with ethyl acetate (3×20 mL) and methylene chloride (15 mL). The combined extracts was washed with brine (20 mL), dried (MgSO$_4$) and concentrated. The crude mixture (90 mg, 78%) was chromatographed over silica gel (10% MeOH, 1% NH$_4$OH in CH$_2$Cl$_2$ followed by 20% MeOH, 2% NH$_4$OH in CH$_2$Cl$_2$) to yield 34.5 mg (31%) of (9R)-9-amino-21-benzylamino-9-deoxo-erythromycin A, 14, [α]$_D$−40.43° (c 1.9, CHCl$_3$); MS m/e 840 (M+1); Anal. (C$_{44}$H$_{77}$N$_3$O$_{12}$) C, H, N; and 43.5 mg (44%) of (9R)-9,21-diamino-9-deoxo-erythromycin A, 15, [α]$_D$−29.08° (c 0.95, MeOH); MS m/e 750 (M+1).

EXAMPLE 13

(9R)-21-(N-benzyl-N-methylamino)-9-deoxo-9-(N,N-dimethylamino)-erythromycin A

Glacial acetic acid (118 μL) was added to a stirring solution of 14 (68 mg, 0.081 mmol) in 5 mL acetonitrile at room temperature. Formalin (37%) (121 μL) was added via syringe. Sodium cyanoborohydride (80 mg, 1.22 mmol) was added and the reaction allowed to stir overnight. The mixture was diluted with MeOH and silica gel (200 mg) was added. The solvent was removed under reduced pressure. The residue was charged onto a silica gel column and eluted with (5% MeOH, 0.5% NH$_4$OH in CH$_2$Cl$_2$ followed by 10% MeOH, 1% NH$_4$OH in CH$_2$Cl$_2$) to yield 66 mg (92%) of compound 16. [α]$_D$−38.2° (c 1.2, MeOH); MS m/e 882 (M+1).

EXAMPLE 14

(9R)-9-deoxo-9-(N,N-dimethylamino)-21-(N-methylamino)-erythromycin A

Palladium hydroxide (50 mg) was added under nitrogen to a stirring solution of 16 (46 mg, 0.052 mmol) in five mL MeOH. The vessel was purged with hydrogen and the solution stirred under 1 atmosphere of hydrogen for five hours, after which the contents were filtered through diatomaceous earth and washed repeatedly with excess CH$_2$Cl$_2$ and MeOH. The combined filtrate and washings were concentrated and then redissolved in 5% NaH$_2$PO$_4$ solution. The solution was adjusted to pH=9.5 with NH$_4$OH and extracted with ethyl acetate (3×15 mL). The combined organic extracts were washed with brine (20 mL), dried (MgSO$_4$) and concentrated. The residue was chromatographed over silica gel (10% MeOH, 1% NH$_4$OH in CH$_2$Cl$_2$) to yield 25 mg (61%) of compound 17, [α]$_D$−34.6° (c 1.2, MeOH); MS m/e 793 (M+1).

EXAMPLE 15

(9R)-9,21-(N,N-dimethylamino)-9-deoxoerythromycin A

Glacial acetic acid (98 μL, 1.34 mmol) and formalin (100 μL, 1.34 mmol) were added to a stirring solution of 15 (50 mg, 0.067 mmol) in 5 mL acetonitrile. Sodium cyanoborohydride (88 mg, 1.34 mmol) was added and the solution stirred at room temperature for twenty-four hours. Methanol was added (5 mL) along with silica gel (200 mg) and the solution evaporated to dryness. The residue was charged onto a column of silica gel and eluted (5% MeOH, 0.5% NH$_4$OH in CH$_2$Cl$_2$ followed by 10% MeOH, 1% NH$_4$OH in CH$_2$Cl$_2$) to yield 58 mg of partially purified material. The material was again chromatographed on silica gel (5% MeOH, 0.5% NH$_4$OH in CH$_2$Cl$_2$) to give 10 mg (18%) of the product 18, [α]$_D$−19.28° (c 1.5, CHCl$_3$); MS m/e 806 (M+1).

EXAMPLE 16

In Vitro Assay of Antibacterial Activity

Representative compounds of the present invention were assayed in vitro for antibacterial activity as follows: Twelve petri dishes containing successive aqueous dilutions of the test compound mixed with 10 ml of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35°-37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each disk was read. The minimum inhibitory concentration (MIC) was defined as the lowest concentration of drug yielding no growth, a slight haze, or sparsely isolated colonies on the inoculum spot as compared to the growth control. The results of this assay, shown below in Tables 1 and 2, support the conclusion that the compounds of the invention are effective antibacterial agents.

TABLE 1

| ORGANISM | STRAIN | | MIC (ug/ml) | | | |
|---|---|---|---|---|---|---|
| | | | 8 | 10 | 11 | 14 |
| STAPHYLOCOCCUS AUREUS | ATCC | 6538P | 0.78 | 25 | 6.2 | 3.1 |
| STAPHYLOCOCCUS AUREUS | A5177 | | 50 | >100 | 100 | >100 |
| STAPHYLOCOCCUS AUREUS | 45 | | 0.78 | 25 | 6.2 | 6.2 |
| STAPHYLOCOCCUS AUREUS | 642A | | 1.56 | 25 | 6.2 | 6.2 |
| STAPHYLOCOCCUS AUREUS | NCTC | 10649 | 0.78 | 12.5 | 6.2 | 3.1 |
| STAPHYLOCOCCUS AUREUS | CMX | 553 | 0.78 | 25 | 6.2 | 6.2 |
| STAPHYLOCOCCUS AUREUS | 1775 | | >100 | >100 | >100 | >100 |
| STAPHYLOCOCCUS EPIDERMIDIS | 3519 | | 0.39 | 25 | 6.2 | 1.56 |
| MICROCOCCUS LUTEUS | ATCC | 9341 | 0.1 | 6.2 | 0.78 | 0.78 |
| MICROCOCCUS LUTEUS | ATCC | 4698 | 0.1 | 3.1 | 0.78 | 3.1 |
| ENTEROCOCCUS FAECIUM | ATCC | 8043 | 0.02 | 12.5 | 1.56 | 3.1 |
| STREPTOCOCCUS BOVIS | A5169 | | 0.02 | 3.1 | 0.78 | 0.2 |
| STREPTOCOCCUS AGALACTIAE | CMX | 508 | 0.05 | 3.1 | 0.78 | 0.39 |
| STREPTOCOCCUS PYOGENES | EES61 | | 0.05 | 1.56 | 0.39 | 0.2 |
| STREPTOCOCCUS PYOGENES | 930 | CONST | >100 | >100 | >100 | >100 |
| STREPTOCOCCUS PYOGENES | 2548 | INDUC | 6.2 | 100 | 50 | 3.1 |
| ESCHERICHIA COLI | JUHL | | 100 | >100 | >100 | 100 |
| ESCHERICHIA COLI | SS | | 0.39 | 1.56 | 0.39 | 0.78 |
| ESCHERICHIA COLI | DC-2 | | 50 | >100 | >100 | 100 |

TABLE 1-continued

| ORGANISM | STRAIN | | MIC (ug/ml) | | | |
|---|---|---|---|---|---|---|
| | | | 8 | 10 | 11 | 14 |
| ESCHERICHIA COLI | H560 | | 25 | 100 | 50 | 25 |
| ESCHERICHIA COLI | KNK | 437 | 50 | >100 | >100 | 100 |
| ENTEROBACTER AEROGENES | ATCC | 13048 | >100 | >100 | >100 | >100 |
| KLEBSIELLA PNEUMONIAE | ATCC | 8045 | 100 | >100 | >100 | 50 |
| PROVIDENCIA STUARTII | CMX | 640 | >100 | >100 | >100 | >100 |
| PSEUDOMONAS AERUGINOSA | BMH10 | | >100 | >100 | >100 | 50 |
| PSEUDOMONAS AERUGINOSA | A5007 | | >100 | >100 | >100 | >100 |
| PSEUDOMONAS AERUGINOSA | K799/WT | | >100 | >100 | >100 | >100 |
| PSEUDOMONAS AERUGINOSA | K799/61 | | 12.5 | 50 | 12.5 | 25 |
| PSEUDOMONAS CEPACIA | 2961 | | >100 | >100 | >100 | >100 |
| ACINETOBACTER CALCOACETICUS | CMX | 669 | 12.5 | >100 | >100 | 50 |

TABLE 2

| ORGANISM | STRAIN | | MIC (ug/ml) | | | |
|---|---|---|---|---|---|---|
| | | | 15 | 16 | 17 | 18 |
| STAPHYLOCOCCUS AUREUS | ATCC | 6538P | 25 | 12.5 | 12.5 | 1.56 |
| STAPHYLOCOCCUS AUREUS | A5177 | | >100 | >100 | >100 | 25 |
| STAPHYLOCOCCUS AUREUS | 45 | | 100 | 6.2 | 6.2 | 1.56 |
| STAPHYLOCOCCUS AUREUS | 642A | | 12.5 | 3.1 | | |
| STAPHYLOCOCCUS AUREUS | NCTC | 10649 | 100 | 12.5 | 6.2 | 1.56 |
| STAPHYLOCOCCUS AUREUS | CMX | 553 | 100 | 12.5 | 12.5 | 3.1 |
| STAPHYLOCOCCUS AUREUS | 1775 | | 100 | 12.5 | >100 | >100 |
| STAPHYLOCOCCUS EPIDERMIDIS | 3519 | | >100 | >100 | 12.5 | 3.1 |
| MICROCOCCUS LUTEUS | ATCC | 9341 | 50 | 6.2 | 1.56 | 0.2 |
| MICROCOCCUS LUTEUS | ATCC | 4698 | 12.5 | 0.39 | 1.56 | 0.78 |
| ENTEROCOCCUS FAECIUM | ATCC | 8043 | 12.5 | 3.1 | 3.1 | 0.39 |
| STREPTOCOCCUS BOVIS | A5169 | | 100 | 1.56 | 0.78 | 0.05 |
| STREPTOCOCCUS AGALACTIAE | CMX | 508 | 12.5 | 0.1 | 1.56 | 0.2 |
| STREPTOCOCCUS PYOGENES | EES61 | | 25 | 0.39 | 0.78 | 0.1 |
| STREPTOCOCCUS PYOGENES | 930 | CONST | 12.5 | 0.78 | >100 | >100 |
| STREPTOCOCCUS PYOGENES | 2548 | INDUC | >100 | 50 | 50 | 25 |
| ESCHERICHIA COLI | JUHL | | 100 | 12.5 | 50 | 12.5 |
| ESCHERICHIA COLI | SS | | >100 | 100 | 0.78 | 0.2 |
| ESCHERICHIA COLI | DC-2 | | 3.1 | 1.56 | 50 | 6.2 |
| ESCHERICHIA COLI | H560 | | >100 | 100 | 12.5 | 3.1 |
| ESCHERICHIA COLI | KNK | 437 | 100 | 50 | 25 | 12.5 |
| ENTEROBACTER AEROGENES | ATCC | 13048 | >100 | 100 | 100 | 25 |
| KLEBSIELLA PNEUMONIAE | ATCC | 8045 | >100 | >100 | 50 | 6.2 |
| PROVIDENCIA STUARTII | CMX | 640 | >100 | 100 | >100 | >100 |
| PSEUDOMONAS AERUGINOSA | BMH10 | | >100 | >100 | 100 | 100 |
| PSEUDOMONAS AERUGINOSA | A5007 | | >100 | 100 | >100 | >100 |
| PSEUDOMONAS AERUGINOSA | K799/WT | | >100 | >100 | >100 | >100 |
| PSEUDOMONAS AERUGINOSA | K799/61 | | >100 | >100 | 3.1 | 1.56 |
| PSEUDOMONAS CEPACIA | 2961 | | 100 | 12.5 | >100 | >100 |
| ACINETOBACTER CALCOACETICUS | CMX | 669 | >100 | >100 | 100 | 12.5 |

The present invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

What is claimed is:

1. A compound having the formula

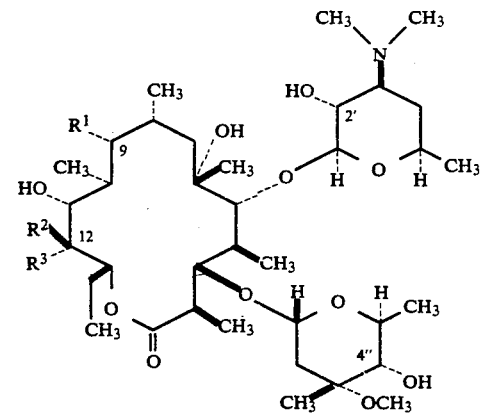

or a pharmaceutically acceptable salt thereof, wherein $R^1$ is $-NR^4R^6$, where $R^4$ and $R^6$ are independently selected from the group consisting of hydrogen, loweralkyl, phenyl(loweralkyl) and naphthyl(loweralkyl) or, together, $R^4$ and $R^6$ form a nitrogen-containing heterocycle attached at the nitrogen atom selected from the group consisting of piperidinyl, morpholinyl, hexahydroazepinyl, azetidinyl, aziridinyl, pyrrolidinyl and piperazinyl and optionally substituted with one or two radicals independently selected from the group consisting of methyl, ethyl, methoxy, amino, halo, hydroxy, nitro and cyano;

$R^2$ is selected from the group consisting of hydrogen, —OH and, when $R^3$ is methylene, oxygen so as to form an epoxide; and $R^3$ is selected from the group consisting of —$NR^4R^6$, —$(CH_2)_nNR^4R^6$ and, when $R^2$ is oxygen, methylene so as to form an epoxide, where n is 1-4 and $R^4$ and $R^6$ are as previously defined, with the proviso that when $R^2$ is —OH, $R^3$ may not be —$NR^4R^6$.

2. A compound according to claim 1 wherein $R^1$ is —$N(CH_3)_2$.

3. A compound according to claim 2 wherein $R^2$ is oxygen and $R^3$ is methylene so as to form an epoxide.

4. A compound according to claim 2 wherein $R^2$ is —OH and $R^3$ is —$CH_2N(CH_3)_2$.

5. A compound selected from the group consisting of
(9R)-9-deoxo-9-(N,N-dimethylamino)-12,21-epoxyerythromycin A,
(9R)-9-amino-21-benzylamino-9-deoxoerythromycin A,
(9R)-9,21-diamino-9-deoxoerythromycin A,
9R)-21-(N-benzyl-N-methylamino)-9-deoxo-9-(N,N-dimethylamino)-erythromycin A,
(9R)-9-deoxo-9-(N,N-dimethylamino)-21-(N-methylamino)-erythromycin A, and
(9R)-9,21-di-(N,N-dimethylamino)-9-deoxoerythromycin A.

6. A compound according to claim 5 selected from the group consisting of
(9R)-9-deoxo-9-(N,N-dimethylamino)-12,21-epoxyerythromycin A and
(9R)-9,21-(N,N-dimethylamino)-9-deoxoerythromycin A.

7. A pharmaceutical composition comprising a therapeutically effective amount of a compound according to claim 1 and a pharmaceutically acceptable carrier.

8. A method for treating bacterial infections in a human or lower mammal, comprising administering to a patient in need of such treatment a therapeutically effective amount of a compound according to claim 1 for such time as is necessary to achieve a therepeutic effect.

* * * * *

UNITED STATES PATENT AND TRADEMARK OFFICE
CERTIFICATE OF CORRECTION

PATENT NO. : 5,217,960

DATED : June 8, 1993

INVENTOR(S) : Paul A. Lartey, Ramin Faghih and Shari DeNinno

Page 1 of 5

It is certified that error appears in the above-indentified patent and that said Letters Patent is hereby corrected as shown below:

On the title page: Item [57] Abstract, please replace

"

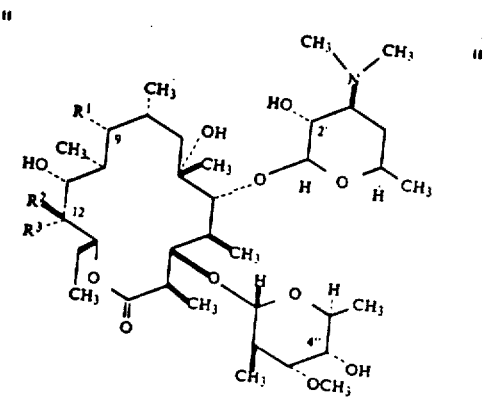

"

with --

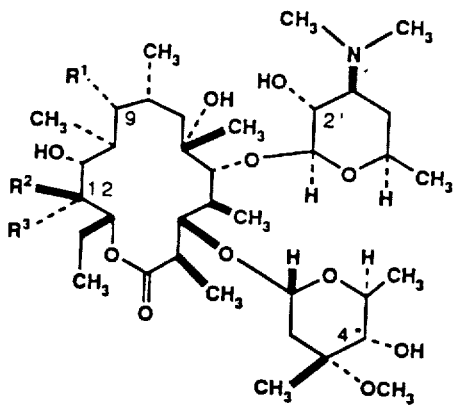

UNITED STATES PATENT AND TRADEMARK OFFICE
CERTIFICATE OF CORRECTION

PATENT NO. : 5,217,960

DATED : June 8, 1993

INVENTOR(S) : Paul A. Lartey, Ramin Faghih and Shari DeNinno

It is certified that error appears in the above-indentified patent and that said Letters Patent is hereby corrected as shown below:

Column 2, structure (II), please replace

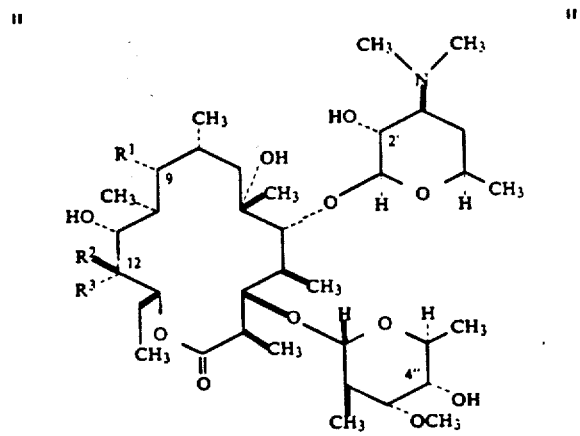

with --

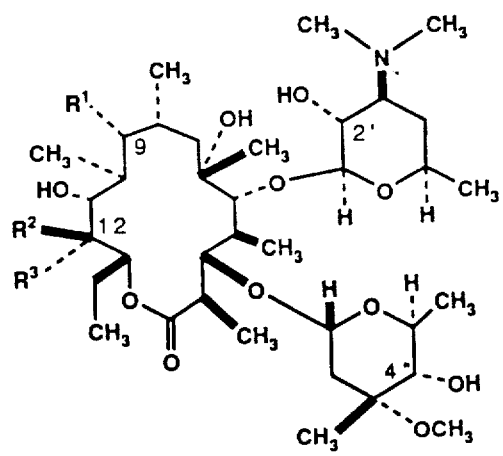

UNITED STATES PATENT AND TRADEMARK OFFICE
CERTIFICATE OF CORRECTION

PATENT NO. : 5,217,960                                    Page 3 of 5
DATED      : June 8, 1993
INVENTOR(S): Paul A. Lartey, Ramin Faghih and Shari DeNinno It is certified that error appears in the above-indentified patent and that said Letters Patent is hereby corrected as shown below:

Column 15, structure 15, please replace

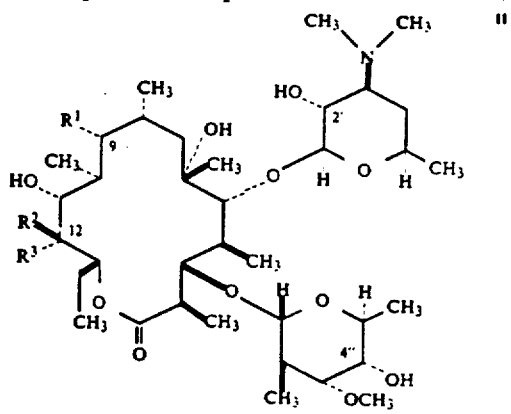

with --

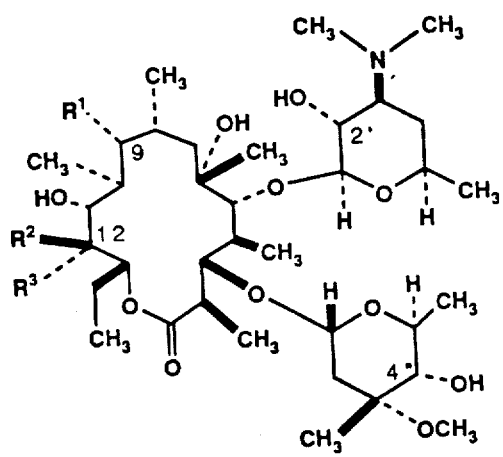

UNITED STATES PATENT AND TRADEMARK OFFICE
CERTIFICATE OF CORRECTION

PATENT NO. : 5,217,960
DATED : June 8, 1993
INVENTOR(S) : Paul A. Lartey, Ramin Faghih and Shari DeNinno It is certified that error appears in the above-indentified patent and that said Letters Patent is hereby corrected as shown below:

Column 16, structure 16, please replace

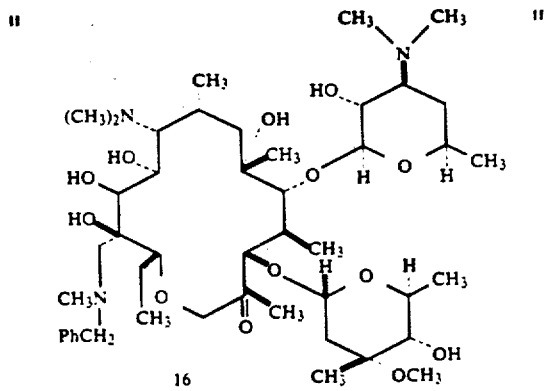

with --

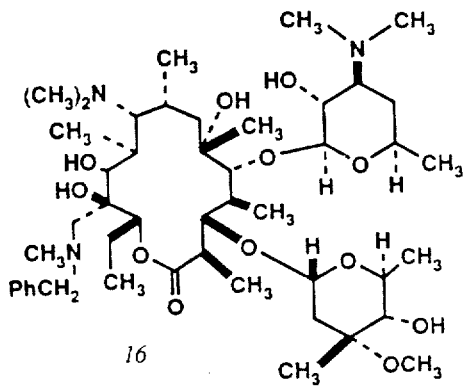

UNITED STATES PATENT AND TRADEMARK OFFICE
CERTIFICATE OF CORRECTION

PATENT NO. : 5,217,960           Page 5 of 5
DATED      : June 8, 1993
INVENTOR(S): Paul A. Lartey, Ramin Faghih and Shari DeNinno It is certified that error appears in the above-indentified patent and that said Letters Patent is hereby corrected as shown below:

Column 16, structure 17, please replace

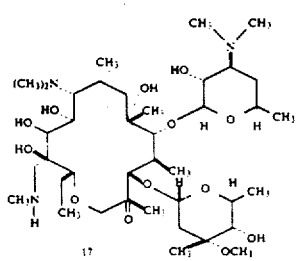

with --

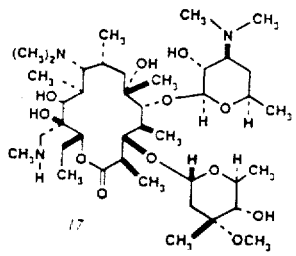

Signed and Sealed this

Twelfth Day of April, 1994

Attest:

BRUCE LEHMAN

*Commissioner of Patents and Trademarks*

*Attesting Officer*